(12) United States Patent
Kato et al.

(10) Patent No.: US 6,200,742 B1
(45) Date of Patent: Mar. 13, 2001

(54) SILVER HALIDE PHOTOGRAPHIC LIGHT-SENSITIVE MATERIAL

(75) Inventors: Yasuhiro Kato; Yasuhiro Shimada; Mario Aoki, all of Minami-Ashigara (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 0 days.

(21) Appl. No.: 09/536,983

(22) Filed: Mar. 29, 2000

(30) Foreign Application Priority Data

Mar. 29, 1999 (JP) .................................................. 11-086883

(51) Int. Cl.[7] .................................................. G03C 1/08
(52) U.S. Cl. ........................................... 430/558; 430/543
(58) Field of Search .................................... 430/505, 543, 430/558

(56) References Cited

U.S. PATENT DOCUMENTS

| 5,118,812 | 6/1992 | Yokoyama et al. . |
| 5,948,607 | 9/1999 | Uchida et al. . |

FOREIGN PATENT DOCUMENTS

| 875470 | 8/1961 | (GB) . |
| 10148921 | 6/1998 | (JP) . |

OTHER PUBLICATIONS

XP002140769—Chemical Abstracts. Registry Handbook—Number Section, 1989 Supplement.

*Primary Examiner*—Geraldine Letscher

(74) *Attorney, Agent, or Firm*—Birch, Stewart, Kolasch & Birch, LLP

(57) ABSTRACT

A silver halide photographic light-sensitive material including a support and at least one light-sensitive layer formed on the support, wherein at least one of the light-sensitive layers contains at least one of the couplers represented by the following formula (I):

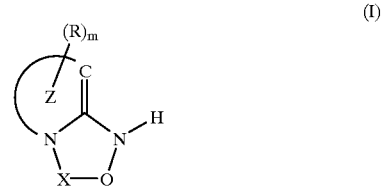

wherein Z represents an atomic group that comprises a carbon atom and/or a nitrogen atom which, together with N—C=C, form a 5- or 6-member aromatic ring; R represents a substituent, and when there are a plurality of R, the R can be same or different, and may be coupled to each other so as to form a fused ring; m represents an integer of from 1 to 4; and X represents a carbonyl group, a methylene group, or a >C=N—Rn group wherein Rn represents a substituent The silver halide photographic light-sensitive material, which has excellent color reproducibility and sharpness and has good color image light-fastness, can be obtained by including therein a coupler which can provide a dye which has excellent hues and storage stability of an image, and whose molar extinction coefficient is high. Also, a method of preparing an azo dye by a coupling reaction of a compound represented by formula (I) and an oxidized p-phenylenediamine derivative is disclosed.

6 Claims, No Drawings

SILVER HALIDE PHOTOGRAPHIC LIGHT-SENSITIVE MATERIAL

BACKGROUND OF THE INVENTION

1. Field of the Invention

The present invention relates to a silver halide photographic light-sensitive material containing therein a coupler which forms a heterocyclic azo dye by a coupling reaction of the coupler and an oxidized developing agent. Further, the present invention relates to a method of preparing a heterocyclic azo dye which can be prepared by this coupling reaction, and to a heterocyclic compound which provides the dye.

2. Description of the Related Art

In a silver halide photographic light-sensitive material (referred to as a "light-sensitive material" in some cases, hereinafter) using a subtractive color process, a color image is formed by dyes of the three primary colors, i.e., yellow, magenta, and cyan. In color photography using an existing p-phenylenediamine-based color-developing agent, a β-acylacetanilide-based compound is used as the yellow coupler. However, hues of the yellow dye obtained from these couplers become reddish, thus making it difficult to obtain yellow hues of high purity. Further, there have been problems in that, since the molar extinction coefficient of the dye is small, a large amount of coupler or silver halide must be used in order to obtain a desired density of the formed color and the film thickness of the light-sensitive material thus becomes larger, and sharpness of the obtained color image thereby deteriorates. Moreover, since this dye has a tendency to decompose under high temperature and/or high humidity, there are problems in image storage stability after the light-sensitive material has been subjected to developing processing. Accordingly, it is desired to improve problems such as those described above.

In order to solve these problems, improvement of an acyl group and an anlide group has been performed. Recently, the 1-alkylcyclopropylcarbonylacetanilide-based compound disclosed in Japanese Patent Application Laid-Open (JP-A) No. 4-218042, the malon di(cyclic amide) coupler disclosed in Japanese Patent Application Laid-Open (JP-A) No. 5-11416, and the like have been proposed as a coupler obtained by improving a conventional acylacetanilide and derivatives thereof. A dye produced from such a coupler has been improved in respect of hues and molar extinction coefficients over conventional dyes. However, the dye is not improved satisfactorily in respect to image storage stability. In addition, since the structure of the coupler has become complicated, the manufacturing cost of the coupler has become expensive thus causing a problem in that such a coupler is less practical.

Instead of a conventional coupler which produces an azomethine dye, the indazole-based compound disclosed in Great Britain Patent No. 875470 has been proposed as a yellow coupler which forms an azo dye having a high extinction coefficient However, since the dye produced by the coupler has an essential problem in that an intramolecular hydrogen bond occurs under neutral condition and the absorption peak or band thereby shifts to higher wavelength, the dye cannot be used practically. Further, as a yellow coupler which forms an azo dye having a high extinction coefficient, there has been proposed the compounds disclosed in JP-A No. 10-148921. However, there is the problem that the pKa of this coupler is so high that the coupling activity of this coupler is insufficient, and when the pKa is lowered in order to improve the coupling activity, the hues deteriorate. As a result, this coupler cannot be used practically.

Further, there has been a strong demand for using azo dyes, whose molecular extinction coefficient is high and which have excellent hues and storage stability, not only for silver halide photographic light-sensitive materials, but also as a general dye, as well as a dye for images including dyes used in inks for ink jet printers. The development of a simple method of preparing an azo dye and in particular, a method of preparing an azo dye using a coupler have been desired.

SUMMARY OF THE INVENTION

In view of the aforementioned facts, it is an object of the present invention to provide a silver halide photographic light-sensitive material, which has excellent color reproducibility and sharpness and satisfactory light-fastness of color images, by including in the light-sensitive material a coupler that provides a dye which has excellent hues, which has a large molar extinction coefficient, and which can provide excellent image storage stability. Further, an object of the present invention is to provide a simple method of preparing an azo dye having a high molecular extinction coefficient and excellent hues and storage stability, and to provide a compound, a dye forming compound, and a dye forming coupler which can form an azo dye by a coupling reaction with an oxidized p-phenylenediamine derivative.

The present inventors conducted various experiments and found that the aforementioned problems can be solved by using a compound which is represented by the following formula (I):

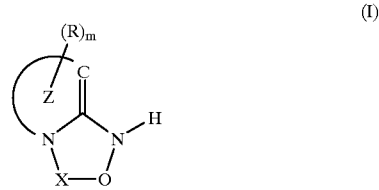

wherein Z represents an atomic group that comprises a carbon atom and/or a nitrogen atom which, together with N—C=C, form a 5- or 6-member aromatic ring; R represents a substituent, and when there are a plurality of R, the R can be same or different, and may be coupled to each other so as to form a fused ring; m represents an integer of from 1 to 4; and X represents a carbonyl group, a methylene group, or a >C=N—Rn group wherein Rn represents a substituent Aspects of the present invention are as follows.

(1) A silver halide photographic light-sensitive material comprising a support and at least one light-sensitive layer formed on the support, wherein at least one of the light-sensitive layers contains at least one of couplers represented by following formula (I):

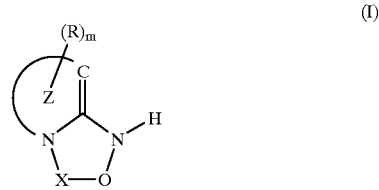

wherein Z represents an atomic group that comprises a carbon atom and/or a nitrogen atom which, together with N—C=C, form a 5- or 6-member aromatic ring; R represents a substituent, and when there are a plurality of R, the R can be same or different, and may be coupled to each other so as to form a fused ring; m represents an integer of from 1 to 4; and X represents a carbonyl group, a methylene group, or a >C=N—Rn group wherein Rn represents a substituent.

(2) The silver halide photographic light-sensitive material described above, wherein the ring formed by Z and N—C=C in the coupler represented by formula (I) is selected from the group consisting of a pyrrole ring, a pyrazole ring, an imidazole ring, a 1,2,3-triazole ring, a pyridine ring a pyridazine ring a pyrimizine ring, a pyrazine ring, an indole ring, an isoindole ring, a benzimidazole ring, a quinoline ring, and an isoquinoline ring.

(3) The silver halide photographic light-sensitive material described above, wherein the coupler represented by the formula (I) is at least one of couplers represented by following formulas (II), (III), (IV), or (V):

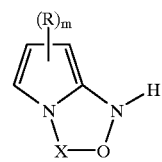
(II)

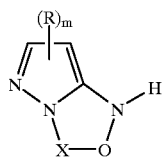
(III)

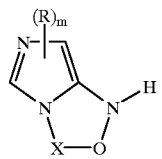
(IV)

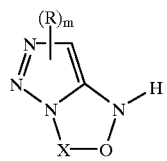
(V)

(4) The silver halide photographic light-sensitive material described above, wherein X of the coupler represented by formula (I) is a carbonyl group.

(5) The silver halide photographic light-sensitive material described above, wherein the amount of the coupler contained in the silver halide photographic light-sensitive material ranges from $1 \times 10^{-3}$ mol to 1 mol per 1 mol of silver halide.

(6) The silver halide photographic light-sensitive material described above, wherein the coupler represented by formula (I) is selected from the group consisting of couplers represented by formula (III) and couplers represented by formula (V).

(7) A compound represented by following formula (I):

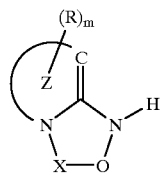
(I)

wherein Z represents an atomic group that comprises a carbon atom and/or a nitrogen atom which, together with N—C=C, form a 5- or 6-member aromatic ring; R represents a substituent, and when there are a plurality of R, the R can be same or different, and may be coupled to each other so as to form a fused ring; m represents an integer of from 1 to 4; and X represents a carbonyl group, a methylene group, or a >C=N—Rn group wherein Rn represents a substituent (8) A method of preparing an azo dye by using a compound represented by following formula (I):

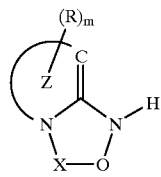
(I)

wherein Z represents an atomic group that comprises a carbon atom and/or a nitrogen atom which, together with N—C=C, form a 5- or 6-member aromatic ring; R represents a substituent, and when there are a plurality of R, the R can be same or different, and may be coupled to each other so as to form a fused ring; m represents an integer of from 1 to 4; and X represents a carbonyl group, a methylene group, or a >C=N—Rn group wherein Rn represents a substituent (9) A method of preparing an azo dye according to claim 8, wherein the compound represented by formula (I) and the compound represented by following formula (A) are used:

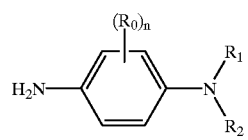
(A)

wherein $R_0$, $R_1$, and $R_2$ each independently represent a substituent, and n is 0 or an integer from 1 to 4.

(10) Use of a compound represented by following formula (I) in the preparation of an azo dye:

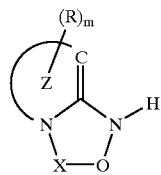
(I)

wherein Z represents an atomic group that comprises a carbon atom and/or a nitrogen atom which, together with N—C=C, form a 5- or 6-member aromatic ring; R represents a substituent, and when there are a plurality of R, the R can be same or different, and may be coupled to each other so as to form a fused ring; m represents an integer of from 1 to 4; and X represents a carbonyl group, a methylene group, or a >C=N—Rn group wherein Rn represents a substituent.

DESCRIPTION OF THE PREFERRED EMBODIMENT

A detailed description of a compound represented by the following formula (I) will be given hereinafter.

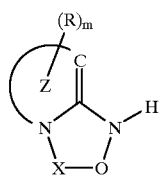
(I)

In formula (I), Z represents an atomic group that comprises a carbon atom and/or a nitrogen atom which, together with N—C=C, form a 5- or 6- member aromatic ring; R represents a substituent, and when there are a plurality of R, the R can be same or different, and may be coupled to each other so as to form a fused ring; m represents an integer of from 1 to 4; and X represents a carbonyl group, a methylene group, or a >C=N—Rn group wherein Rn represents a substituent.

In formula (I), examples of the 5- or 6- member aromatic ring formed by Z and N—C=C include: a pyrrole ring; a pyrazole ring; an imidazole ring; a 1,2,3-triazole ring; a pyridine ring; a pyridazine ring; a pyrimidine ring, a pyrazine ring; an indole ring, an isoindole ring; a benzmidazole ring; a quinoline nng; an isoquinoline ring; and the like.

The carbon atom and/or nitrogen atom which are comprised of the atomic group represented by Z form a skeleton of the 5- or 6-member aromatic ring and may bond to a hydrogen atom or a substituent. In this case, Z comprises the hydrogen atom or substituent as well as the carbon atom and/or the nitrogen atom.

In formula (I), examples of substituents represented by R include: an aliphatic group; an aromatic group; an acyl group; an alkoxycarbonyl group; an aryloxycarbonyl group; an acylamino group; an alkylthio group; an arylthio group; a heterocyclic group; a sulfonyl group; a halogen atom; a nitro group; a nitroso group; a cyano group; a carboxyl group; a hydroxyl group; a sulfonamide group; an alkoxy group; an aryloxy group; an acyloxy group; a carbamoyl group; an amino group; a ureide group; a sulfamoyl group; a carbamoylsulfonyl group; a hydrazinyl group; an azo group; a sulfonyloxy group; a carbamoyloxy group; a sulfamoyloxy group; a heterocyclic oxy group; a heterocyclic thio group; and the like. In a case in which there are a plurality of R (in a case in which m is an integer of from 2 to 4), the R can be same or different, and can be coupled to each other so as to form another saturated or unsaturated cyclic ring having 5 to 6 members. These groups may be substituted by a substituent. Examples of the substituent are the groups listed above.

In formula (I), X represents a carbonyl group, a methylene group, or a >C=N—Rn group, and preferably represents a carbonyl group. In a case in which X is >C=N—Rn, Rn is selected from the same substituents as those listed above for R. A preferable example of X is an aliphatic group or an aromatic group.

In formula (I), each of R and Rn, and the methine group in a case in which X represents a methylene group, can be further substituted by substituents. Examples of the substituents include the same substituents as those listed above for R.

A more detailed description of the compound which is used in the present invention and which is represented by formula (I) will be given hereinafter.

Compounds represented by the following formulas (II), (III), (IV), or (V) are examples of a compound which is represented by formula (I) and in which a heterocyclic ring is a preferable example of the aromatic ring having 5 to 6 members and formed by Z and N—C=C.

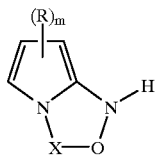
(II)

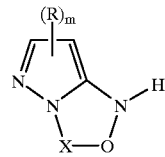
(III)

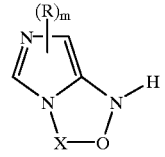
(IV)

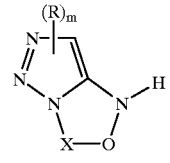
(V)

Among the formulas (II), (III), (IV), and (V), X and R represent the same substituents as defined for formula (I). Further, m represents an integer of from 1 to 3.

More specifically, in formulas (II), (III), (IV), and (V), m preferably represents an integer of from 1 to 3 in formula (II), 1 or 2 in formulas (III) and (IV), and 1 in formula (V).

In formulas (II) through (V), the compound represented by formula (II), (III) or (V) is preferable, and the compound represented by formula (III) or (V) is more preferable.

Specific examples of the substituent R include: an aliphatic group (preferably an alkyl group having 1 to 30 carbon atoms, an alkenyl group having 2 to 30 carbon atoms, an alkynyl group having 2 to 30 carbon atoms, a cycloalkyl group having 3 to 30 carbon atoms or a cycloalkenyl group having 3 to 30 carbon atoms; for example, a methyl group, an ethyl group, an n-propyl group, an isopropyl group, a t-butyl group, a cyclohexyl group, or the like); an aromatic group (preferably an aryl group having 6 to 30 carbon atoms, for example, a substituted or unsubstituted phenyl group, or the like); a halogen atom (fluorine, chlorine, bromine, or the like); a cyano group; an alkoxy group (preferably an alkoxy group having 1 to 30 carbon atoms, for example, ethoxy, methoxycarbonylmethoxy, carboxypropyloxy, methanesulfonylethoxy, perfluoropropoxy, or the like); an aryloxy group (preferably an aryloxy group having 6 to 30 carbon atoms, for example, 4-carboxyphenoxy, 4-(4-hydroxyphenylsulfonyl) phenoxy, 4-methanesulfonyl-3-carboxyphenoxy, 2-methanesulfonyl-4-acetylsulfamoylphenoxy, or the like); an acyloxy group (preferably an acyloxy group having 1 to 30 carbon atoms, for example, acetoxy, benzoyloxy, formyloxy, or the like); a sulfonyloxy group (preferably an alkylsulfonyl group having 1 to 30 carbon atoms or an arylsulfonyl group having 6 to 30 carbon atoms, for example, methanesulfonyloxy, benzenesulfonyloxy, or the like); an acylamino group (preferably an acylamino group having from 1 to 30 carbon atoms, for example, heptafluorobutyrylamino, benzoylamino, or the like); a sulfonamide group (preferably an alkanesulfonamide group having 1 to 30 carbon atoms or an arylsulfonamide group having 6 to 30 carbon atoms, for example, methanesulfonamide, benzenesulfonamide, or the like); an alkoxycarbonyloxy group (preferably an alkoxycarbonyloxy group having 2 to 30 carbon atoms, for example, ethoxycarbonyloxy, or the like); a carbamoyloxy group preferably a carbamoyloxy group having 1 to 30 carbon atoms, for example, diethylcarbamoyloxy, piperidinocarbonyloxy, morpholinocarbonyloxy, or the like); an alkylthio group (preferably an alkylthio group having 1 to 30 carbon atoms, for example, 2-carboxyethylthio, or the like); an arylthio group (preferably an arylthio group having 6 to 30 carbon atoms, for example, 2-octyloxy-5-t-octylphenylthio, 2-(2,4di-t-amylphenoxy) butyrylaminophenylthio, or the like); a heterocyclic thio group (preferably a heterocyclic thio group having 1 to 30 carbon atoms, for example, 1-phenyltetrazolylthio, 2-benzimidazolylthio, or the like); a heterocyclic oxy group (preferably a heterocyclic oxy group having 1 to 30 carbon atoms, for example, 2-pyridyloxy, 5-nitro-2-pyridyloxy, or the like); a nitrogen-containing heterocyclic group having 5 or 6 members (preferably a nitrogen-containing heterocyclic group having 5 or 6 members and containing 1 to 30 carbon atoms, and more preferably, a heterocyclic group having, as the ring forming atoms, at least one nitrogen atom, as well as atoms selected from the group consisting of nitrogen atoms, oxygen atoms, sulfur atoms, and carbon atoms, for example, 1-imidazolyl, 1-pyrazolyl, 5-chloro-1-tetrazolyl, 1-benzotriazolyl, 2-phenylcarbamoyl-1-imidazolyl, 5,5-dimethylhydantoin-3-yl, 1-benzylhydantoin-3-yl, 5,5-dimethyloxazolidine-2,4-dione-3-yl, or the like); an azo group (preferably an arylazo group containing from 6 to 30 carbon atoms or a heterocyclic azo group containing from 1 to 30 carbon atoms, for example, a heterocyclic azo group 4-methoxyphenyl azo, 4-pivaloylaminophenyl azo, or the like); a carbamoyl group (preferably a carbamoyl group having from 1 to 30 carbon atoms, for example, a diethylcarbamoyl, a phenylcarbamoyl, a morpholinocarbamoyl, and the like), a sulfamoyl group preferably a sulfamoyl group having from 0 to 30 carbon atoms, for example, a methylsulfamoyl, a phenylsulfamoyl, and the like), and the like. Further, adjacent Rs may bond together so as to form a ring which ring may be an aliphatic ring an aromatic ring, or a heterocyclic ring, and is preferably a 5- or 6-member ring, for example, a benzene ring, a furan ring, a thiophene ring, a cyclopentane ring, or a cyclohexane ring. When two Rs bond together, they may form a methylene dioxy group. The ring formed by two Rs and the ring formed by Z and N—C=C form a fused ring.

Each of R, as well as the ring formed by Rs bonding together, may be further substituted by a substituent (Examples of the substituent are the above-listed examples of the substituents for R.)

It is preferable that the sum total of the carbon atoms of R(s) and Rn is 2 to 50, and more preferably 8 to 45, and even more preferably 15 to 40. The number of carbon atoms of R(s) and Rn is 1 to 30, preferably 6 to 30, even more preferably 8 to 30, and most preferably 10 to 25.

Preferable groups among these groups are aliphatic groups (especially alkyl groups), aromatic groups (especially aryl groups), halogen atoms, cyano groups, alkoxy groups, aryloxy groups, acyloxy groups, acylamino groups, alkoxycarbonyl group, alkylthio groups, carbamoyl groups, and sulfamoyl groups. Further, two Rs may bind together so as to form a benzene ring.

Among the compounds represented by formula (I) in the present invention, preferable specific examples are shown below. However, the present invention is not limited to these examples.

(1)

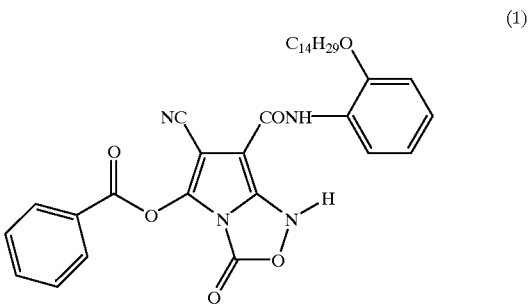

(2)

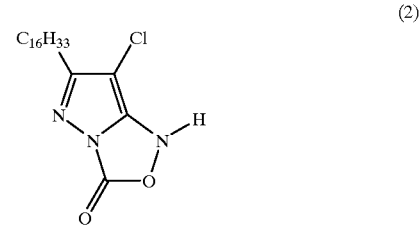

(3)

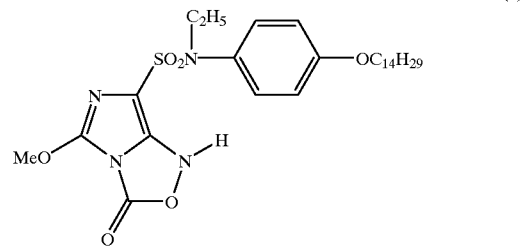

(4)

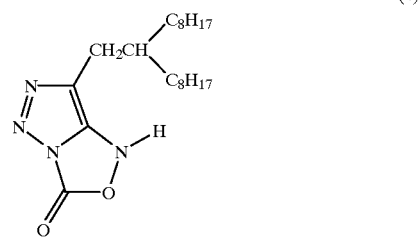

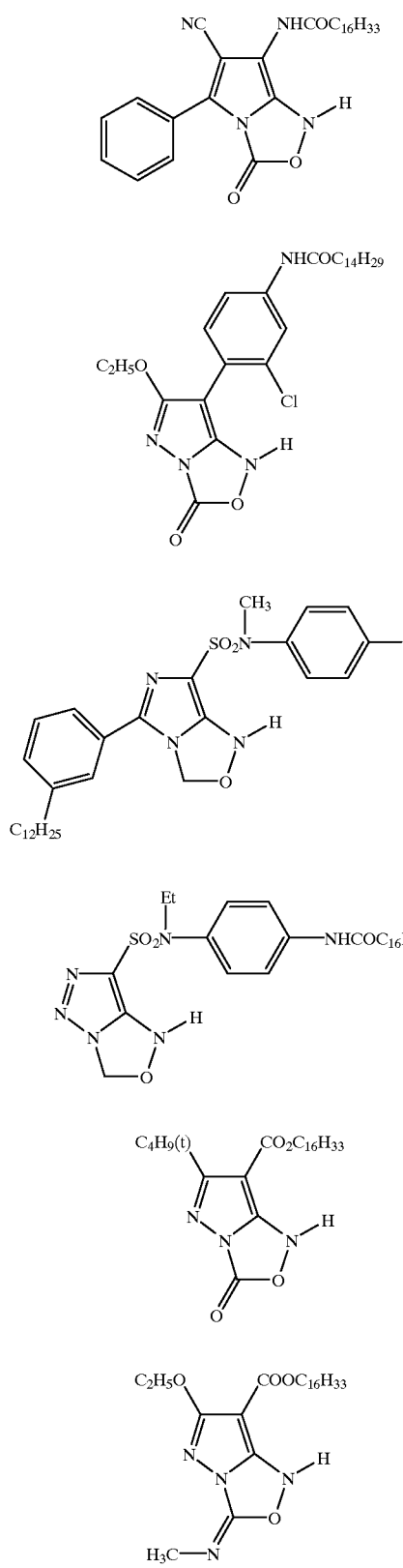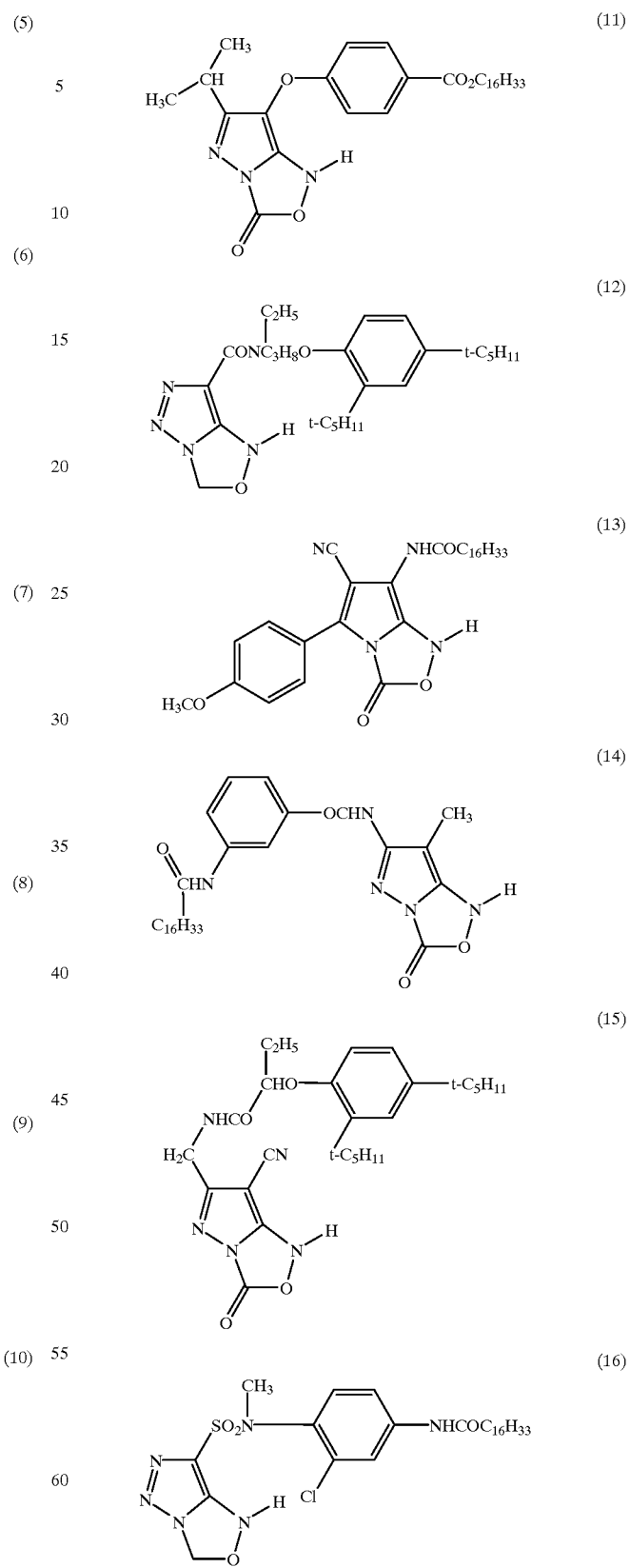

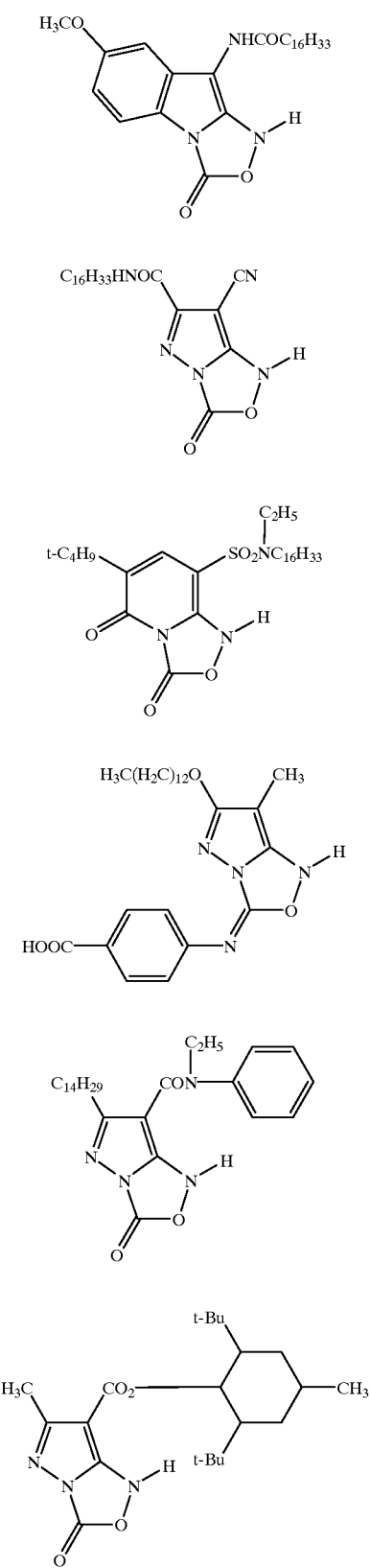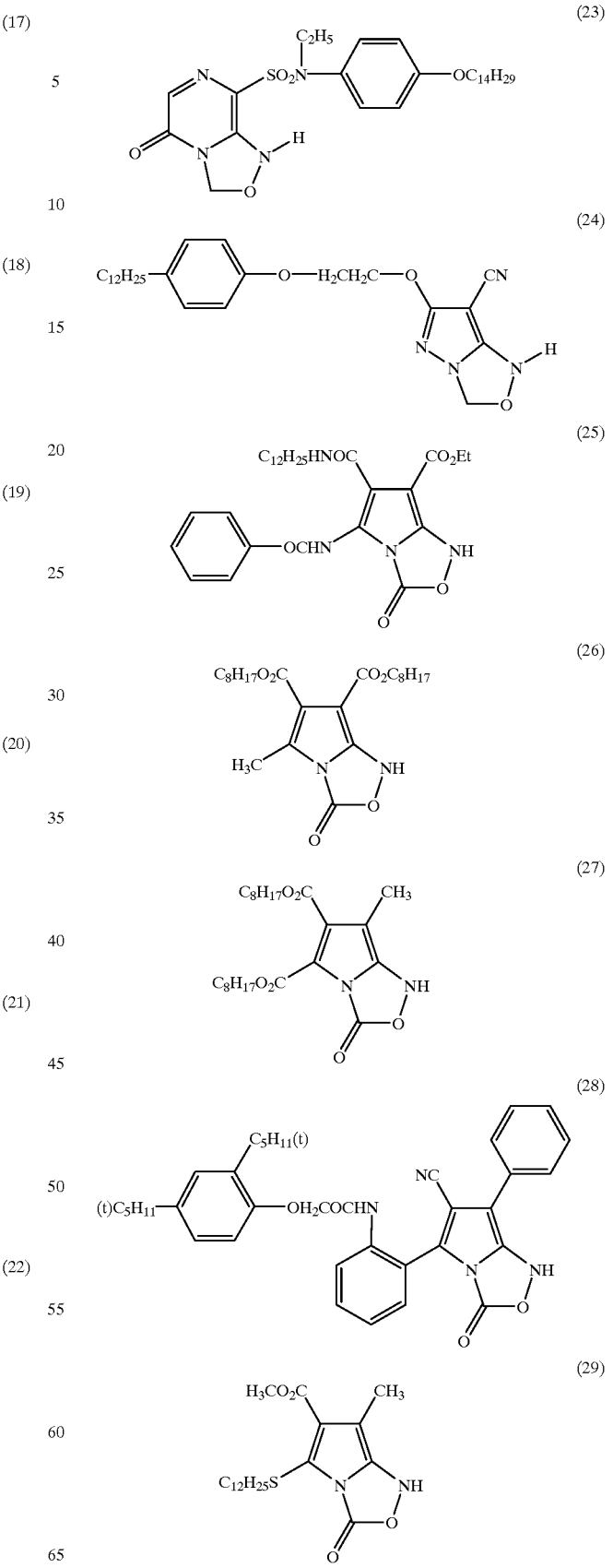

(30) 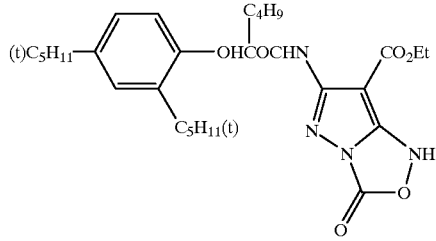

(31) 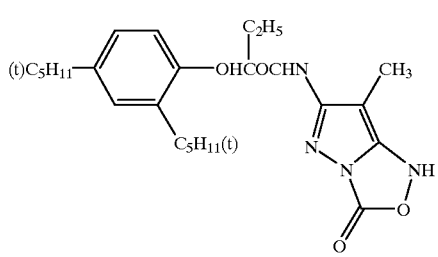

(32) 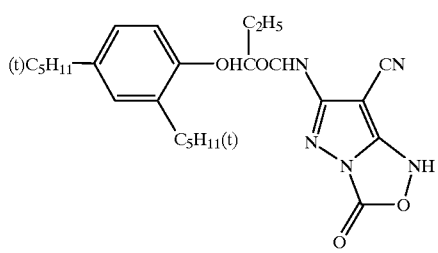

(33) 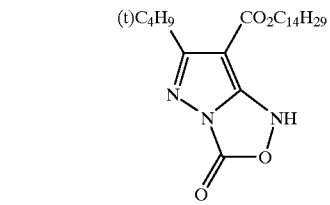

(34) 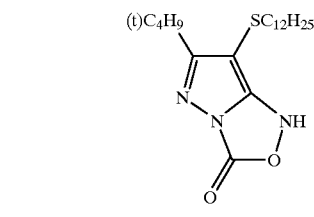

(35) 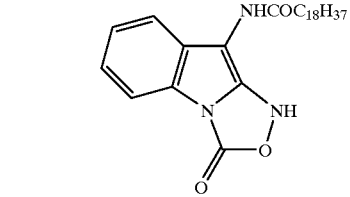

(36)

(37)

(38)

(39)

In the following explanation, when one of the compounds illustrated above as preferable examples is mentioned, it will be designated by the above number in parentheses next to the coupler or compound, i.e., a coupler or compound designated by (x) above will be referred to hereinafter as "coupler or compound (x)".

Specific synthesis examples of the compound represented by formula (I) are shown below:

Synthesis Example 1: Synthesis of Compound (1)

Compound (1) can be synthesized via the route shown below:

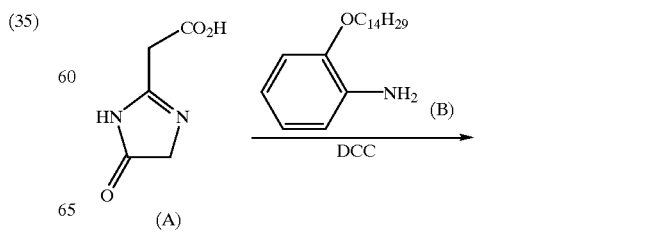

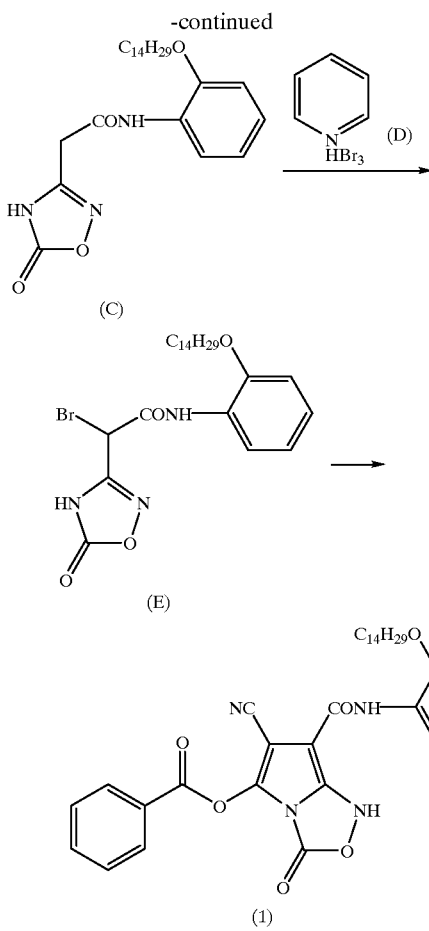

(C)

(E)

(1)

A compound (A) (0.35 g) and a compound (B) (0.9 g) were dissolved in N,N-dimethylacetoamide (DMAc) (5 ml). Into the obtained solution, dicyclohexylcarbonamide (DCC) (0.56 g) was added by drops at room temperature. After the reaction took place, the precipitated dicyclohexylurea was filtered out from the reaction solution. To the obtained filtrated solution was added ethyl acetate (20 ml), and the resultant solution was washed with water. After an organic phase was dried by using magnesium sulfate, ethyl acetate was removed, and the residue was purified by column chromatography, thus obtaining a compound (C) (0.33 g).

The compound (C) (0.5 g) was dissolved in tetrahydrofuran (5 ml), and to the resulting solution was added a compound (D) (0.71 g). The reaction of these compounds was carried out for two days at room temperature. After the reaction was completed, to the reaction solution was added ethyl acetate (20 ml), and the resultant solution was washed with water. After the organic phase was dried, ethyl acetate was removed under reduced pressure, thus obtaining a compound (E).

On the other hand, a 28% methanol solution of sodium methylate (0.94 g) was added to a dimethylacetoamide solution (5 ml) containing 0.5 g of methyl cyanoacetate, and this mixed solution was stirred for one hour. The resultant solution is referred to as (S).

The aforementioned obtained compound (E) (0.66 g) was dissolved in dimethylacetoamide (5 ml). The resultant solution was slowly added by drops to the solution (S) which was in an ice bath. After the reaction was completed, to the reaction solution was added ethyl acetate (20 ml), and the resultant mixture was washed with water. After the organic phase was dried, ethyl acetate was removed under reduced pressure. To the residue were added methanol (5 ml) and water (1 ml), as well as potassium hydroxide (0.1 g). After the resultant mixture was left to stand for one day, to the mixture was added ethyl acetate (20 ml), and then hydrochloric acid. The resultant mixture was neutralized, and then washed with water. After the organic phase was dried, ethyl acetate was removed under reduced pressure. To the residue was added pyridine (5 ml), and then benzoyl chloride (0.5 g), and a reaction was carried out at room temperature. After the reaction, to the reaction solution was added ethyl acetate (20 ml), and the resultant solution was washed with water. After the organic phase was dried, ethyl acetate was removed under reduced pressure, and the residue was purified by using column chromatography to thereby obtain a compound (1) (0.2 g).

Synthesis Example 2: Synthesis of compound (2)

A compound (2) can be synthesized via the route shown below:

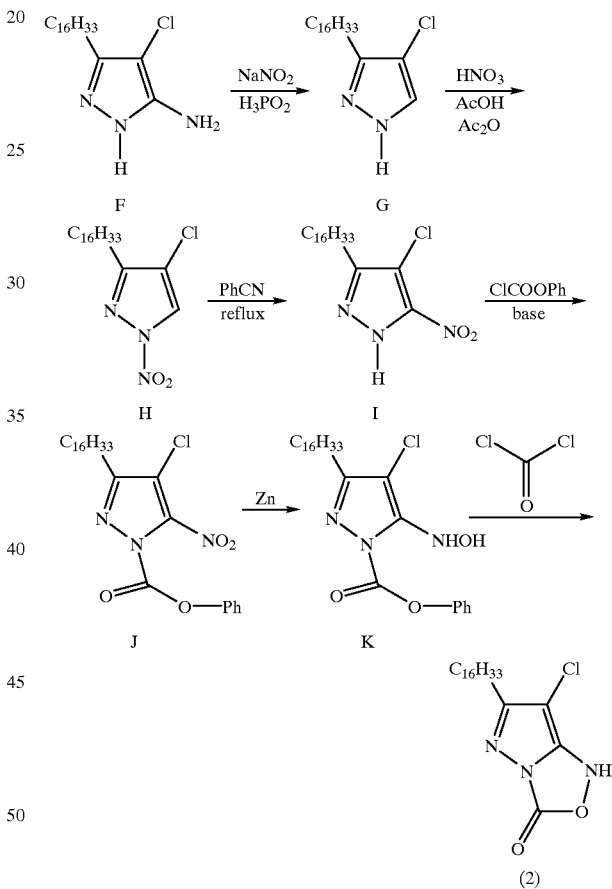

(2)

A compound F (10.3 g) was added to 30% $H_3PO_2$ (160 ml), and the resultant solution was cooled to an internal temperature of 5° C. To this solution, an aqueous solution of sodium nitrite (which was prepared by dissolving sodium nitrite (4.6 g) in water (20 ml)) was added slowly by drops. The resultant solution was stirred for two hours at room temperature. Thereafter, the reaction solution was neutralized by an aqueous solution of sodium hydroxide. The product was extracted by using acetonitrile and salt water. After an acetonitrile phase was dried by using magnesium sulfate, magnesium sulfate was removed by filtration, and the solvent was removed under reduced pressure to thereby obtain a compound (G) (9.6 g).

The compound (G)(2.05 g) was added to acetic acid (6 ml), and the resultant solution was cooled by using frozen salt water. To the resultant solution, fuming nitric acid (1.05 ml) was added slowly by drops while the internal temperature was maintained at 30° C. or less. Further, acetic anhydride (4 ml) was added slowly by drops while the internal temperature was maintained at 30° C. or less. After this dropwise addition, it was confirmed that the obtained solution had become clear, and the external temperature was set at room temperature (the reaction vessel was taken out from the frozen salt water bath). The resultant solution was stirred for three hours at room temperature. Thereafter, the obtained reaction solution was poured into ice-water. While continuing stirring, the solution was neutralized by potassium carbonate until the pH of the solution became 7. The precipitated crystals were filtrated, thus obtaining a compound (H)(2.03 g).

The compound (H)(2 g) was added to benzonitrile (4 ml), and the resultant mixture was refluxed for two hours at an external temperature of 200° C. After the reaction was completed, to the resultant mixture were added ethyl acetate and water, and the organic phase was extracted, washed with water, and dried. Thereafter, the solvent was removed under reduced pressure, thus obtaining a compound (I) (1.94 g).

The compound (I) (1.5 g) was dissolved in N,N-dimethylacetoamide (DMAc; 15 ml), and to the resultant solution was added NaOMe (0.22 g). Phenyl chloroformate (0.70 g) was slowly added thereto by drops. After the reaction was carried out for three hours at a temperature of 50° C., to the resultant mixture were added ethyl acetate and water. The organic phase was extracted, washed with water, and dried. The solvent was removed under reduced pressure to thereby obtain a compound (J) (1.38 g).

Zinc powder (180 g, 2.75 mol) was suspended in 50% ethanol (500 mL), and the compound (J) (1.2 g) was added while stirring vigorously. An ammonium chloride solution was added slowly by drops. After boiling calmed down, a zinc compound was removed by using a glass filter, and the filtrated solution was cooled by a freezing mixture to thereby obtain a compound (K) (1.09 g).

The compound (K)(1.00 g) was dissolved in THF (5 mL), and to the resultant solution was added triphosgene (0.62 g). After the resultant mixture was stirred for three hours at room temperature, the solvent was removed to concentrate the reaction solution under reduced pressure. Ethylacetate and water were added, and an organic phase was extracted. After the organic phase was washed with water and dried, ethylacetate was removed under reduced pressure. The residue was purified by using silica gel column chromatography to thereby obtain a white crystal L (0.67 g) which was the compound (2).

The light-sensitive material of the present invention may comprise a support, and on the support, at least one layer that contains a coupler which is a compound represented by formula (I). The coupler is contained in a hydrophilic colloidal layer formed of an ordinary gelatin binder. The light-sensitive material of the present invention can be structured by applying light-sensitive emulsion layers (i.e., light-sensitive layers) which are a blue-sensitive silver halide emulsion layer, a green-sensitive silver halide emulsion layer, and a red-sensitive silver halide emulsion layer, one by one, onto the support, in any arbitrary order. Further, instead of one of the aforementioned light-sensitive emulsion layers, an infrared light-sensitive silver halide emulsion layer can be used. A silver halide emulsion which has sensitivity in a wavelength range of the light-sensitive silver halide emulsion layer, and a coupler for forming a dye which has a complementary color relationship with the light sensed by the layer are contained in each of the light-sensitive silver halide emulsion layers so that color reproduction by using the subtractive color process can be carried out However, a silver halide emulsion and a coupler for forming a dye which does not have a complementary color relationship with the light sensed by the emulsion may be used in the same layer.

In a conventional color light-sensitive material in which p-phenylenediamines are used as a color developing agent, the compound which is used in the present invention and which is represented by formula (I) is mainly useful as a yellow or magenta coupler, and is particularly useful as a yellow coupler. However, the coupler used in the present invention can be contained in any of the light-sensitive emulsion layers (preferably, the blue-sensitive silver halide emulsion layer or the green-sensitive silver halide emulsion layer, and more preferably, the blue-sensitive silver halide emulsion layer). The coupler used in the present invention is also useful as a dye forming coupler that provides a dye of various hues even in a system using a color developing agent other than the aforementioned p-phenylenediamines.

The amount of the coupler used in the present invention which is added to the light-sensitive material preferably ranges from $1 \times 10^{-3}$ mol to 1 mol per 1 mol of silver halide, and more preferably ranges from $2 \times 10^{-3}$ mol to $3 \times 10^{-1}$ mol per 1 mol of silver halide.

The coupler used in the present invention can be introduced into a light-sensitive material by various known dispersion methods. However, an oil droplet-in-water dispersion method in which a coupler is dissolved in a high boiling point organic solvent (a low boiling point organic solvent can be used in combination therewith) is emulsified in an aqueous solution of gelatin, and then the resultant dispersion is added to a silver halide emulsion is preferably used.

An example of a high boiling point solvent used in the oil droplet-in-water dispersion method is disclosed in U.S. Pat. No. 2,322,027. Specific examples of a latex dispersion method which is a polymer dispersion method are disclosed in U.S. Pat. No. 4,199,363, German Patent (OLS) No. 2541274, Japanese Patent Application Publication (JP-B) No. 53-41091, European Patent Application Nos. 0727703A1 and 0727704A1, and the like. Further, a dispersion method using an organic solvent soluble polymer is disclosed in PCT International Publication No. WO88/723.

Examples of the high boiling point organic solvents which can be used in the oil droplet-in-water dispersion method include: phthalate esters (dibutyl phthalate, dioctyl phthalate, di-2-ethylhexyl phthalate, and the like), phosphate or phosphonate esters (triphenyl phosphate, tricresyl phosphate, tri-2-ethylhexyl phosphate, and the like), fatty esters (di-2-ethylhexyl succinate, tributyl citrate, and the like), benzoate esters (2-ethylhexyl benzoate, dodecyl benzoate, and the like), amides (N,N-diethyldodecane amide, N,N-dimethylolein amide, and the like), alcohols or phenols (isostearyl alcohol, 2,4-di-tert-amylphenol, and the like), anilines (N,N-dibutyl-2-butoxy-5-tert-octylaniine, and the like), chlorinated paraffins, hydrocarbons (dodecylbenzene, diisopropylnaphthalene, and the like), carboxylic acids (2-(2,4-di-tert-amylphenoxy), butyric acids, and the like. Further, as a co-solvent, an organic solvent whose boiling point is 30° C. or more and 160° C. or less (ethyl acetate, butyl acetate, methyl ethyl ketone, cyclohexanone, methyl cellosolve acetate, dimethyl formamide, or the like) can be used in combination with the high boiling point organic solvent The high boiling point organic solvent is preferably used in a weight ratio of 0 to 10 times and preferably 0 to 4 times the weight of the coupler.

The silver halide photographic light-sensitive material of the present invention can contain other conventionally known photographic materials or additives.

For example, as a photographic support, a transmissive support or a reflective support can be used. As the transmissive support, it is preferable to use a transparent film such as a cellulose nitrate film, polyethylene terephthalate film, or the like, and a support in which an information recording layer such as a magnetic layer is provided on a polyester formed by 2,6-naphthalene dicarboxylic add (NDCA) and ethylene glycol (EG), a polyester formed by NDCA and terephthalic acid and EG, or the like. As a reflective support, it is preferable to use a support which is laminated with a plurality of layers formed by water proof resin such as polyethylene or polyester and which contains a white pigment such as titanium oxide or the like in at least one of the laminated layers.

Further, it is preferable for the aforementioned waterproof resin layer to contain a fluorescent brightener. Moreover, the fluorescent brightener may be dispersed in the hydrophilic colloidal layer in the light-sensitive material. As the fluorescent brightener, preferably, benzoxazole, coumarin, and pyrazoline, and derivatives of these compounds can be used, and more preferably, benzoxazolyl naphthalene and derivatives thereof, and benzoxazolyl stilbene and derivatives thereof can be used. Further, the amount of the fluorescent brightener used is not particularly limited, but preferably ranges from 1 to 100 mg/m$^2$. When the fluorescent brightener is mixed into the waterproof resin layer, the mixture ratio of the fluorescent brightener with respect to the waterproof resin preferably ranges from 0.0005 to 3 wt %, and more preferably ranges from 0.001 to 0.5 wt. %.

As the reflective support, it is possible to use a support in which a hydrophilic colloidal layer containing a white pigment therein is applied to a transmissive support or to a reflective support such as described above.

Further, the reflective support may be a support having a speculator reflective- or a second-type diffusion reflective metal surface.

As silver halide emulsions used in the present invention, a silver chloride emulsion, a silver bromide emulsion, a silver iodobromide emulsion, a chloro (iodo) bromide emulsion, and the like are used. However, from the standpoint of rapid processing capability, a silver chloride emulsion or a chlorobromide emulsion whose silver chloride content is at least 95 mol % is preferable. Further, a silver halide emulsion whose silver chloride content is at least 98 mol % is more preferable. Among such silver halide emulsions, those having silver bromide localized phases on the surfaces of silver chloride particles are particularly preferable because high light-sensitivity can be obtained, and stabilization of photographic performance can also be improved.

The reflective supports, silver halide emulsions, plural types of metal ions which are doped in silver halide particles, storage stabilizers or anifoggants of silver halide emulsions, chemical sensitizing methods (sensitizers), spectral sensitizing methods (spectral sensitizers), cyan, magenta, and yellow couplers and the emulsion and dispersion methods thereof, color image storability modifiers (stain inhibitors or fading inhibitors), dye (colored layers), types of gelatin, layer structures of the light-sensitive material and pH of the film of the light-sensitive material which are described in the publications listed in Table 1 can be preferably applied to the present invention.

TABLE 1

| Elements | JP-A No. 7-104448 | JP-A No. 7-77775 | JP-A No. 7-301895 |
|---|---|---|---|
| Reflective support | line 12 of 7$^{th}$ col. to line 19 of 12$^{th}$ col. | line 43 of 35$^{th}$ col. to line 1 of 44$^{th}$ col. | line 40 of 5$^{th}$ col. to line 26 of 9$^{th}$ col. |
| Silver halide emulsion | line 29 of 72$^{nd}$ col. to line 18 of 74$^{th}$ col. | line 36 of 44$^{th}$ col. to line 29 of 46$^{th}$ col. | line 48 of 77$^{th}$ col. to line 28 of 80$^{th}$ col. |
| plural types of metal ions | line 19 of 74$^{th}$ col. to line 44 of the same col. | line 30 of 46$^{th}$ col. to line 5 of 47$^{th}$ col. | line 29 of 80$^{th}$ col. to line 6 of 81$^{st}$ col. |
| Storage stabilizer or antifoggant | line 9 of 75$^{th}$ col. to line 18 of the same col. | line 20 of 47$^{th}$ col. to line 29 of the same col. | line 11 of 18$^{th}$ col. to line 37 of 31$^{st}$ col. (especially mercapto heterocyclic ring compound) |
| Chemical sensitizing method (chemical sensitizer) | line 45 of 74$^{th}$ col. to line 6 of 75$^{th}$ col. | line 7 of 47$^{th}$ col. to line 17 of the same col. | line 9 of 81$^{st}$ col. to line 17 of the same col. |
| Spectral sensitizing method (spectral sensitizer) | line 19 of 75$^{th}$ col. to line 45 of 76$^{th}$ col. | line 30 of 47$^{th}$ col. to line 6 of 49$^{th}$ col. | line 21 of 81$^{st}$ col. to line 48 of 82$^{nd}$ col. |
| Cyan coupler | line 20 of 12$^{th}$ col. to line 49 of 39$^{th}$ col. | line 50 of 62$^{nd}$ col. to line 16 of the same col. | line 49 of 88$^{th}$ col. to line 16 of 89$^{th}$ col. |
| Yellow coupler | line 40 of 87$^{th}$ col. to line 3 of 88$^{th}$ col. | line 17 of 63$^{rd}$ col. to line 30 of the same col. | line 17 of 89$^{th}$ col. to line 30 of the same col. |
| Magenta coupler | line 4 of 88$^{th}$ col. to line 18 of the same col. | line 3 of 63$^{rd}$ col. to line 11 of 64$^{th}$ col. | line 34 of 31$^{st}$ col. to line 44 of 77$^{th}$ col. and line 32 of 88$^{th}$ col. to line 46 of the same col. |
| Emulsion and dispersion method of couplers | line 3 of 71$^{st}$ col. to line 11 of 72$^{nd}$ col. | line 36 of 61$^{st}$ col. to line 49 of the same col. | line 35 of 87$^{th}$ col. to line 48 of the same col. |
| Color image storability modifier (stain inhibitor) | line 50 of 39$^{th}$ col. to line 9 of 70$^{th}$ col. | line 50 of 61$^{st}$ col. to line 49 of 62$^{nd}$ col. | line 49 of 87$^{th}$ col. to line 48 of 88$^{th}$ col. |
| Fading inhibitor | line 10 of 70$^{th}$ col. to line 2 of 71$^{st}$ col. | | |
| Dye (colored layer) | line 42 of 77$^{th}$ col. to line 41 | line 14 of 7$^{th}$ col. to line 42 | line 27 of 9$^{th}$ col. to line 10 of |

TABLE 1-continued

| Elements | JP-A No. 7-104448 | JP-A No. 7-77775 | JP-A No. 7-301895 |
| --- | --- | --- | --- |
| | of 78th col. | of 19th col. and line 3 of 50th col. to line 14 of 51st col. | 18th col. |
| Types of gelatin | line 42 of 78th col. to line 48 of the same col. | line 15 of 51st col. to line 20 of the same col. | line 13 of 83rd col. to line 19 of the same col. |
| Layer structure of light-sensitive material | line 11 of 39th col. to line 26 of the same col. | line 2 of 44th col. to line 35 of the same col. | line 38 of 31st col. to line 33 of 32nd col. |
| pH of film of light-sensitive material | line 12 of 72nd col. to line 28 of the same col. | | |
| Scanning exposure | line 6 of 76th col. to line 41 of 77th col. | line 7 of 49th col. to line 2 of 50th col. | line 49 of 82nd col. to line 12 of 83rd col. |
| Preservative in developer | line 19 of 88th col. to line 22 of 89th col. | | |

Also useful as cyan, magenta and yellow couplers which are used in the present invention are the couplers which are disclosed in JP-A Nos. 62-215272 (from line 4 of the upper right column on page 91 to line 6 of the upper left column on page 121), and 2-33144 (from line 14 of the upper right column on page 3 to the last line of the upper left column on page 18 and from line 6 of the upper right column on page 30 to line 11 of the lower right column on page 35), and in European Patent Application No. 0355660A2 (lines 15 to 27 on page 4, line 30 on page 5 to the final line on page 28, lines 29 to 31 on page 45, and line 23 on page 47 to line 50 on page 63).

As an anti-bacterial agent or an antimold agent which can be used in the present invention, those disclosed in JP-A No. 63-271247 are useful. As a hydrophilic colloid which is used for the light-sensitive emulsion layer which forms the light-sensitive material, gelatin is preferable. Especially, a heavy metal which is contained in gelatin as impuities such as iron, copper, zinc, or manganese is preferably 5 ppm or less, and more preferably 3 ppm or less.

In addition to print systems using an ordinary negative printer, the light-sensitive material of the present invention is also applicable to scanning exposure systems using a cathode ray tube (CRT).

As compared to an exposure device using a laser, a CRT exposure device is more simple and more compact, and can be manufactured inexpensively. Further, adjustment of the light axis and color is easy.

A CRT which is used for image exposure employs various luminophors which emit light in spectral regions as needed. For example, one of red, green, and blue luminophors is used, or two or more are used in combination. The spectral region is not limited to the aforementioned red, green, and blue, and instead, fluorescent substance which emits light of the yellow, orange, and violet colors, or infrared region may be used. In particular, a CRT in which these luminophors are used to thereby emit white color light is often used.

In a case where the light-sensitive material has a plurality of light-sensitive layers each having a different spectral sensitivity distribution, and the CRT has a fluorescent substance which emits light of a plurality of the spectral regions, the light-sensitive material can be exposed to a plurality of colors at one time. Namely, a plurality of color image signals can be inputted to the CRT so that light can be emitted from the tube surface. Alternatively, an exposure method (sequential surface exposure) can be adopted in which an image signal for each color is input to the CRT in a sequential order so that the CRT emits light whose wavelength corresponds to the color of the inputted image signal and the light-sensitive material is exposed by the light which passes through a film which cuts colors other than color of the light Generally, this sequential surface exposure is preferable because it can use a CRT of high resolution thus allowing for high quality images.

In the light-sensitive material of the present invention, it is preferable to use a digital scanning exposure system using monochromatic high density light such as a gas laser, an LED (light emitting diode), a semiconductor laser, a second harmonic generator (SHG) in which a semiconductor laser or a solid-state laser which uses a semiconductor laser as an excitation light source and a nonlinear optical crystal are used in combination, or the like. In order to make the system more compact and less expensive, it is preferable to use a semiconductor laser, or a second harmonic generator (SHG) in which a semiconductor laser or a solid-state laser and a nonlinear optical crystal are used in combination. In particular, in order to design an exposure device which is compact, inexpensive, has a long life, and has excellent stability, it is preferable to use a semiconductor laser, and it is preferable to use a semiconductor laser as at least one of the exposure light sources.

In a case in which such a light source for scanning exposure is used, the spectral sensitivity peak wavelengths of the light-sensitive material of the present invention can be arbitrarily set by the wavelengths of the light sources used for scanning exposure. In the second harmonic generator (SHG) obtained by using a solid-state laser using a semiconductor laser as the excitation light source or a semiconductor and a nonlinear optical crystal in combination, since an oscillation wavelength of the laser can be reduced to ½, blue color light and green color light can be obtained. Accordingly, the spectral sensitivity peak wavelengths of the light-sensitive material can be set to be in the three ordinary wavelength regions of blue, green, and red.

The exposure time is preferably $10^{-4}$ sec. or less, and more preferably $10^{-6}$ sec. or less, wherein the exposure time in such scanning exposure is defined as the time for exposing a pixel when the pixel density is 400 dpi.

Preferable examples of the scanning exposure system which can be applied to the light-sensitive material of the present invention are described in more detail in the publications listed in above Table 1.

In order to process the light-sensitive material of the present invention, the processing materials and processing methods which are disclosed in JP-A Nos. 2-207250 (from line 1 of the lower right column on page 26 to line 9 of the upper right column on page 34) and 497355 (from line 17 of the upper left column on page 5 to line 20 of the lower right column on page 18) can be preferably applied. Further, as a preservative used for a developer which is employed to process the light-sensitive material of the present invention, compounds which are described in the publications listed in above Table 1 are preferably used.

Examples of methods in which the exposed light-sensitive material of the present invention is developed include a wet developing method such as a method using a conventional developer containing an alkaline agent and developing agent, an activator method using an activator solution such as alkaline solution which does not contain a developing agent and used for developing the light sensitive material containing a developing agent, a heat developing method which does not utilize a processing solution, or the like. Especially, the activator method is preferable because control and handling of the processing solution which does not contain a developing agent is facilitated, and an amount of waste solution which may affect the environment adversely is reduced.

In the activator method, as a developing agent or a precursor thereof which is contained in the light-sensitive material, hydrazine compounds which are disclosed in JP-A Nos. 8-234388, 9-152686, 9-152693, 9-160193, and 9-211814 are preferable.

A developing method in which an image amplification process (intensification process) using hydrogen peroxide is performed is preferably used to process the light-sensitive material containing a small amount of silver. In particular, it is preferable to apply this method to the activator method. More specifically, image forming methods using an activator solution containing hydrogen peroxide and disclosed in JP-A Nos. 8-297354 and 9-152695 are preferably employed.

In the activator method, after the light-sensitive material has been processed by using the activator solution, usually, a process for removing silver is carried out However, in the image amplification processing method using a light-sensitive material having a small amount of silver, the process of removing silver may be omitted, and instead, a simple method such as a washing-in-water process or a stabilizing process can be applied. Further, in a case in which image information is read from the light-sensitive material by a scanner or the like, even when a light-sensitive material having a large amount of silver such as a light-sensitive material for photographing is used, a silver removal process can be omitted.

As processing materials such as the activator solution, the silver removal solution (bleaching and/or fixing solution), and the rinsing solution and stabilization solution, and processing methods using the materials which are used in the present invention, known methods or materials can be used. Those disclosed in Research Disclosure, Item No. 36544 (September 1994), pages 536 to 541, and in JP-A No. 8-234388 can preferably be used.

The light-sensitive material of the present invention can also preferably be used as a light-sensitive material for an advanced photographic system having a magnetic recording layer. Further, the light-sensitive material of the present invention can also preferably be applied to a heat-developing system using a small amount of water and a completely dry system in which a heat-developing process is performed without using any water at all. Examples of these systems are disclosed in JP-A Nos. 6-35118, 6-17528, 56-146133, 60-119557, and 1-161236.

In the present invention, the silver halide photographic light-sensitive material is not only light-sensitive materials for forming color images, but also includes light-sensitive materials for forming monochrome images including black and white images.

When the coupler of the present invention is applied to a color paper, a structure and the other components of the color paper are disclosed in, for example, JP-A-11-7109. In particular, the disclosure of paragraphs 0071 through 0087 of JP-A-11-7109 are incorporated by reference herein.

When the coupler of the present invention is applied to a color negative film, a structure and the other components of the color negative film are disclosed in, for example, JP-A-11-305396. The disclosure of paragraphs 0115 through 0217 of JP-A-11-305396 is incorporated by reference herein.

When the coupler of the present invention is applied to a color reversal film, a structure and the other components of the color reversal film are disclosed in JP-A-11-84601. The disclosure of paragraphs 0018 through 0021 of JP-A-11-84601 is incorporated by reference herein.

The compound represented by formula (I) of the present invention is useful not ordy as a dye forming coupler, but also as an intermediate which provides an azo dye. The obtained azo dye has excellent hues, a high molecular extinction coefficient, and good storage stability, and is useful as a dye for images and as a dyestuff.

More detailed explanation is given hereinafter.

The compound represented by formula (I) is useful for synthesizing an azo dye. More specifically, due to the coupling reaction between the compound of formula (I) and an oxidized p-phenylenediamine derivative, especially an oxidized N,N-di-substituted-p-phenylenediamine derivative, an azo dye can easily be obtained. In this way, there is the advantage that an azo dye can be manufactured without going through a diazo coupling reaction which has complicated operations and is effected by a diazonium salt Namely, as can be seen from the following formulas, due to the compound expressed by general formula (I) and the compound expressed by general formula (A), the dye expressed by general formula (D) can be obtained easily in one process.

The reaction takes place as follows. First, the hydrogen atom is dissociated from the nitrogen atom bonded to the X—O— in the compound represented by general formula (I), and a coupling reaction takes place between this portion and the oxidant which is generated by oxidizing the compound represented by general formula (A) by an oxidizing agent. Thereafter, the X—O portion breaks-off, so that the azo dye of general formula (D) is obtained. The present reaction is characterized in that the oxidant obtained from the compound represented by general formula (A) reacts with the nitrogen atom, and that due to this reaction, a five-member ring cleaves. The X—O⁻ or the X—OH bonded to the nitrogen ring included in the ring represented by Z breaks off from the nitrogen atom. Due to the X—O⁻ or the X—OH breaking off from the nitrogen atom, the performances of the dye are greatly improved, which is the object of the present invention.

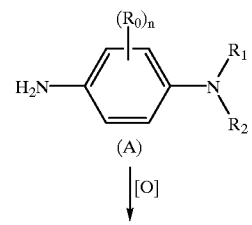

(A)

↓[O]

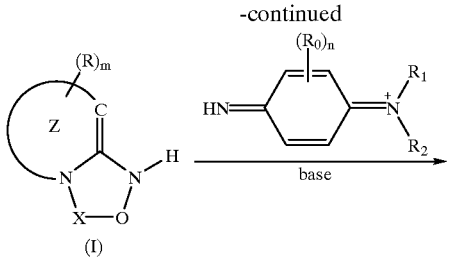

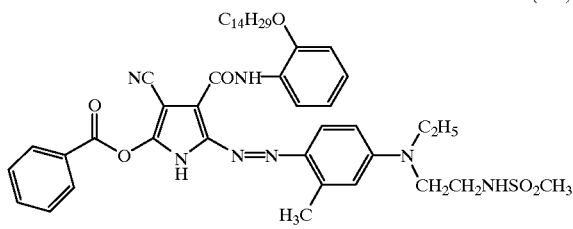

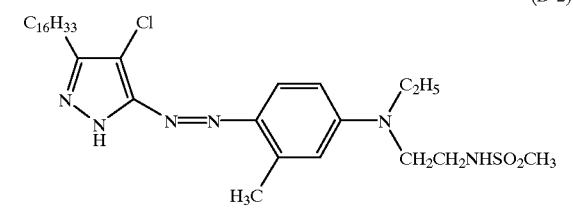

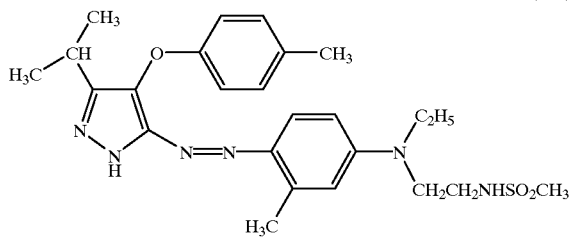

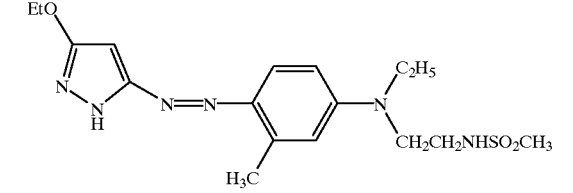

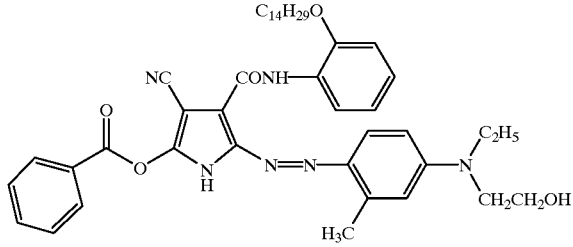

Here, in general formula (D), $R_0$, $R_1$, and $R_2$ each independently represent a substituent, and n is 0 or an integer from 1 to 4. R, Z and m are the same as those in formula (I).

Examples of the substituent represented by $R_0$, $R_1$, and $R_2$ are groups which are the examples for R in general formula (I). $R_0$ is preferably a substituted or unsubstituted alkyl group having from 1 to 30 carbon atoms, a substituted or unsubstituted alkenyl group having from 1 to 30 carbon atoms, a substituted or unsubstituted aryl group having from 6 to 30 carbon atoms, a substituted or unsubstituted alkoxy group having from 1 to 30 carbon atoms, or a halogen atom. $R_1$ and $R_2$ are preferably a substituted or unsubstituted alkyl group having from 1 to 30 carbon atoms or a substituted or unsubstituted aryl group having from 6 to 30 carbon atoms. It is preferable that n is 0 or 1.

More preferably, $R_0$ is an unsubstituted alkyl group having from 1 to 4 carbon atoms, and $R_1$ and $R_2$ are a substituted or unsubstituted alkyl group having from 1 to 4 carbon atoms. A hydroxyl group and a methanesulfonylamino group are preferable examples of substituents.

Especially preferably, $R_0$ is a methyl group, $R_1$ is an ethyl group, and $R_2$ is a β-methanesulfonamidoethyl group or a β-hydroxyethyl group.

As will be described in the following Examples, the azo dye represented by formula (D) can be easily synthesized by dissolving in a solvent the coupler represented by formula (I) and the p-phenylenediamine derivative represented by formula (A), and by adding an oxidizing agent to this solution. Examples of the $R_0$, $R_1$, and $R_2$ in formula (A) are the same as the examples of the $R_0$, $R_1$, and $R_2$ in general formula (D).

Any solvent that can dissolve the compound represented by formula (I) and the compound represented by formula (A) can be used regardless of its polarity or non-polarity. Examples include chloroform, ethyl acetate, ethanol, N,N-dimethylformamide, and the like. The amount of the compound represented by general formula (A) with respect to the compound represented by general formula (I) is, in a molar ratio, 0.1 to 10, preferably 0.5 to 5, and more preferably 0.8 to 1.5. Examples of the base which can be used are sodium carbonate, potassium carbonate, sodium hydrogencarbonate, potassium hydrogencarbonate, sodium hydroxide, potassium hydroxide, and the like. The base is used in an amount which is sufficient to dissociate the compound represented by formula (I). In the case that the compound represented by formula (A) is a salt, the base is used in the sum of the amount described above and an amount which is needed to remove a base bonded to the salt. Any oxidizing agent can be used in this reaction, and examples thereof are persulfate, manganese dioxide, silver halide, ferric chloride, and the like. The reaction temperature is −10 to 100° C., preferably room temperature to 80° C., and more preferably room temperature to 50° C.

The following dyes represented by general formula (D) are examples, but the present invention is not to be limited to these examples.

-continued

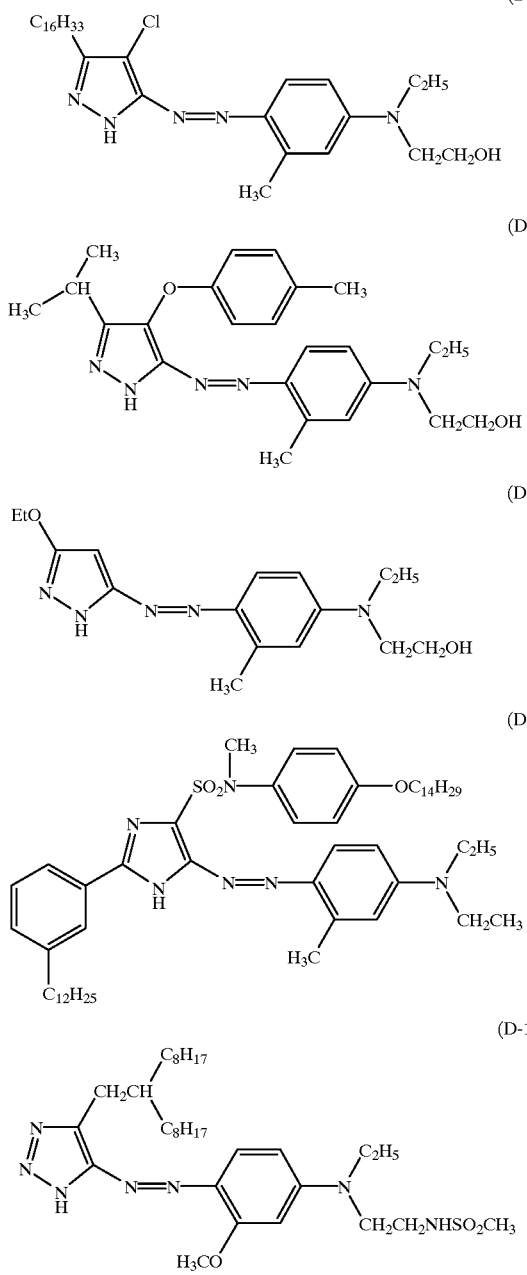

Due to the aforementioned excellent characteristics, these dyes are useful not only as dyes for a color photographic light-sensitive material, but also as dyes for images, inks, and general dyes.

EXAMPLES

A more detailed description of the present invention will be given hereinafter with reference to Examples. However, the present invention is not limited to these Examples.

[Comparative Example 1]

1. Preparation of comparative dye (CD-1)

A solution in which ammonium persulfate (1.45 g) was dissolved in water (10 ml) was gradually added to a mixture of the following comparative coupler (C-1) (0.85 g), N-ethyl-N-(β-methanesulfonamidoethyl)-3-methyl-4-aminoaniline sulfate) (0.80 g), sodium carbonate (3.75 g), chloroform (60 ml), and water (50 ml) while stirring at room temperature. After the mixture was stirred for one hour, a chloroform phase was separated from the mixture, and purified by silica gel chromatography, thus obtaining the following comparative dye (CD-1) which was a yellow azomethine dye.

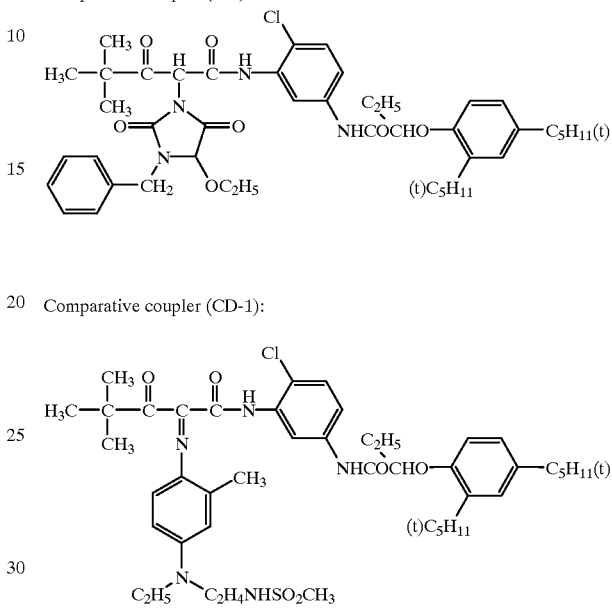

2. Preparation of emulsion of the comparative coupler (C-1)

The comparative coupler (C-1) (0.88 g) and tricresyl phosphate (2.6 g) were dissolved in ethyl acetate (10 ml) while heating was carried out (the resultant mixture is referred to as an "oil phase solution".)

Separately, gelatin (4.2 g) was added to water (25 ml) at room temperature, and was sufficiently swelled. This mixture was then heated to a temperature of 40° C., and was completely dissolved. To the resultant gelatin aqueous solution were added a 5% aqueous solution of sodium dodecyl benzene sulfonate (3 ml) and the oil phase solution that was prepared in advance, while the gelatin solution was kept at a temperature of about 40° C. The resultant mixture was emulsified by using a homogenizer thus preparing an emulsion.

3. Preparation of light-sensitive material for comparison

A coating solution having the following composition was prepared by using the emulsion of the obtained comparative coupler (C-1). The coating solution was coated on a polyethylene laminated paper having a subbing layer so as to provide the coupler in an amount of 1 mmol/m². Further, gelatin was coated on this layer to an amount of 2 g/m², thus preparing a sample 201 as a light-sensitive material for comparison.

| (Composition of coating solution) | |
|---|---|
| emulsion: silver chlorobromide (Br 30 mol %) | 13 g |
| 10% aqueous solution of gelatin | 28 g |
| emulsion of comparative coupler (C-1) | 22 g |
| water | 37 ml |

| (Composition of coating solution) | |
|---|---|
| 4% aqueous solution of sodium 1-hydroxy-3,5-dichloro-s-triazine | 5 ml |

[Examples 1 to 4]

1. Preparation of dyes (D-1) to (D-4)

The following dyes D-1 (using coupler (1)), D-2 (using coupler (2)), D-3 (using coupler (37)), and D-4 (using coupler (38)), which are azomethine dyes, were synthesized in the same manner as in Comparative Example 1 except that the comparative coupler (C-1) was replaced by each of the exemplified couplers (1), (2), (37), and (38), in the "1. Preparation of the comparative dye (CD-1)" in Comparative Example 1.

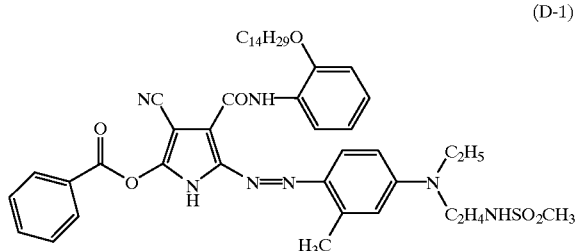
(D-1)

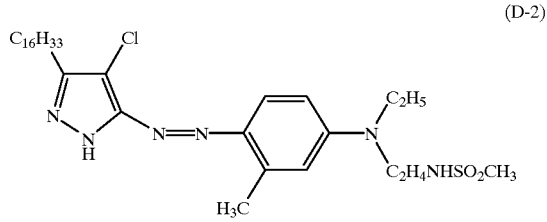
(D-2)

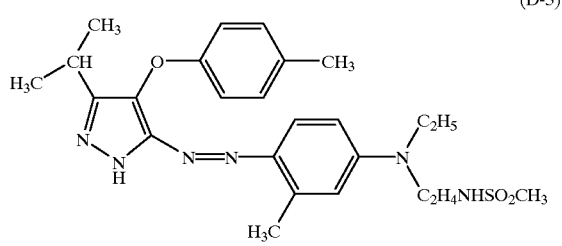
(D-3)

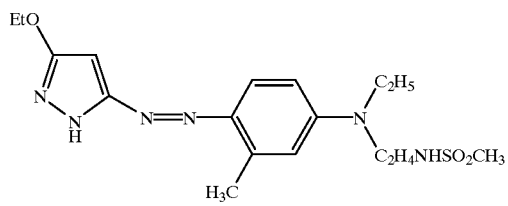
(D-4)

2. Preparation of emulsions of couplers (1), (2), (37) and (38)

Emulsions of the couplers were prepared in the same manner as in Comparative Example 1 except that the comparative coupler (C-1) was replaced by the couplers (1), (2), (37), and (38) exemplified in the present invention, in the "2. Preparation of emulsion of the comparative coupler (C-1)" in Comparative Example 1.

3. Preparation of light-sensitive materials of the present invention

A sample 202 (using coupler (1)), a sample 203 (using coupler (2)), a sample 204 (using coupler (37)), and a sample 205 (using coupler (38)) as light-sensitive materials of the present invention were prepared in the same manner as in Comparative Example 1 except that the emulsion of the comparative coupler (C-1) was replaced by the emulsions of the exemplified couplers (1), (2), (37), and (38), in the "3. Preparation of light-sensitive material for comparison" in Comparative Example 1.

[Measurement of molar extinction coefficient]

Molar extinction coefficients of the comparative dye (CD-1), and the dyes (D-1) to (D4) which were obtained in the above-described Comparative Example and Examples were measured as follows:

For each of the comparative dye (CD-1) and the dyes (D-1) to (D-4), 1.5 mg of the dye was measured and charged into a 100 ml messflask. Ethyl acetate (100 ml) was added to the content of the flask and the content was dissolved. The resultant solution was diluted with ethyl acetate thus preparing sample solutions 101 (using the comparative dye (CD-1)), 102 (using the dye (D-1)), 103 (using the dye (D-2)), 104 (using the dye (D-3)), and 105 (using the dye (D-4).

For each of the obtained sample solutions 101 to 105, the sample solution was charged into a quartz cell having a thickness of 1 cm, and a visible absorption spectrum was measured by an ultraviolet and visible spectrophotometer (manufactured by Shimazu Corp.), and a molar extinction coefficient was calculated. Molar extinction coefficients are shown in following Table 2.

TABLE 2

| | Sample solution No. | Type of coupler | Type of dye | Molar extinction coefficient |
|---|---|---|---|---|
| Comp. Example 1 | 101 | Comparative Coupler (C-1) | CD-1 | $1.65 \times 10^4$ |
| Example 1 | 102 | Coupler (1) | D-1 | $2.18 \times 10^4$ |
| Example 2 | 103 | Coupler (2) | D-2 | $2.34 \times 10^4$ |
| Example 3 | 104 | Coupler (37) | D-3 | $2.36 \times 10^4$ |
| Example 4 | 105 | Coupler (38) | D-4 | $2.44 \times 10^4$ |

From the results of Table 2, it can be seen that the molar extinction coefficient of each of the dyes obtained from the couplers in the present invention was large as compared to that of the dye obtained from the comparative coupler. Due to the above fact, the light-sensitive material of the present invention can provide the same density as a conventional light-sensitive material even by using a thinner layer. This means that color reproducibility and sharpness of the obtained image of the silver halide photographic light-sensitive material of the present invention can be improved.

[Color image light-fastness evaluation test]

A color image light-fastness evaluation test was carried out on each of the samples 201 to 205 which were obtained in the above-described Comparative Example and Examples.

First, each sample was wedge-exposed through irradiation of white light thereon, and a color developing process was performed by following the processing steps listed below.

| (Processing steps) | | |
|---|---|---|
| Step | Temperature | Processing time |
| Color development | 35° C. | 3 min. |
| Bleaching and/or fixing | 30 to 36° C. | 45 sec. |
| Stabilization (1) | 30 to 37° C. | 20 sec. |
| Stabilization (2) | 30 to 37° C. | 20 sec. |
| Stabilization (3) | 30 to 37° C. | 20 sec. |
| Drying | 70 to 85° C. | 60 sec. |

The steps of color development, bleaching and/or fixing, stabilization (1), stabilization (2), and stabilization (3) were performed by immersing each sample into each of the processing solutions described below under the aforementioned conditions.

| (Color developer in color-developing process) | |
|---|---|
| water | 800 ml |
| ethylenediaminetetraacetic acid | 2.0 g |
| triethanolamine | 8.0 g |
| sodium chloride | 1.4 g |
| potassium bromide | 0.6 g |
| potassium carbonate | 25 g |
| N-ethyl-N-(β-methanesulfonamidoethyl)-3-methyl-4-aminoaniline sulfate | 5.0 g |
| N,N-diethylhydroxylamine | 4.2 g |
| 5,6-dihydroxybenzene-1,2,4-trisulfonate | 0.3 g |
| fluorescent brightener WHITEX 4 (manufactured by Sumitomo Chemical Co., Ltd.) | 2.0 g |

The mixture having the aforementioned composition was diluted with water such that the amount of the diluted solution was 1000 ml. This solution was used as the color developer. The obtained color developer had a pH of 10.25 (at a temperature of 25° C.).

| (Bleaching and/or fixing solution in bleaching and/or fixing process) | |
|---|---|
| water | 400 ml |
| aqueous solution of ammonium thiosulfate (700 g/liter) | 100 ml |
| sodium sulfite | 18 g |
| iron (III) ammonium ethylenediaminetetraacetate | 55 g |
| disodium ethylenediaminetetraacetate | 3 g |
| acetate | 8 g |

The resultant mixture having the aforementioned composition was diluted with water such that the amount of the diluted solution was 1000 ml. This solution was as the bleaching and/or fixing solution. The obtained bleaching and/or fixation solution had a pH of 5.5 (at a temperature of 25° C.).

| (Stabilization solution in stabilization steps (1) to (3)) | |
|---|---|
| formalin (37%) | 0.1 g |
| formalin sulfite adduct | 0.7 g |
| 5-chloro-2-methyl-4-isothiazoline-3-one | 0.02 g |
| 2-methyl-4-isothiazoline-3-one | 0.01 g |
| copper sulfate | 0.005 g |

The resultant mixture having the aforementioned composition was diluted with water such that the amount of the diluted solution was 1000 ml. This solution was used as the stabilization solution. The obtained stabilization solution had a pH of 4.0 (at a temperature of 25° C.).

A fading test was performed on each of the samples 201 to 205, for which the color developing process had been completed, under the conditions that each sample was subjected to irradiation over a period of 14 days (wherein the irradiation was intermittent with light being irradiated for 5 hours and then not being irradiated for 1 hour) by using an "Xe" light source of 100,000 Lux.

The density of the formed color of each sample before and after the fading test was measured by a TCD-type densitometer (manufactured by Fuji Photo Film Co., Ltd.). The ratio (a residue ratio: %) of the density of the formed color after the fading test to the density of the formed color before the fading test was calculated, and the result was used as the evaluation index of color image light-fastness. Results are shown in Table 3.

TABLE 3

| | Sample No. of light-sensitive material | Type of coupler | Type of dye | Residue Rate (%) |
|---|---|---|---|---|
| Comp. Example 1 | 201 | Comparative Coupler (C-1) | CD-1 | 45 |
| Example 1 | 202 | Coupler (1) | D-1 | 68 |
| Example 2 | 203 | Coupler (2) | D-2 | 73 |
| Example 3 | 204 | Coupler (37) | D-3 | 55 |
| Example 4 | 205 | Coupler (38) | D-4 | 64 |

As can be seen from Table 3, the light-sensitive materials of the present invention have excellent light-fastness.

[Comparative Example 2]

A sample 301 as a light-sensitive material was prepared in the same manner as in Comparative Example 1 except that, in the emulsion, instead of the silver chlorobromide (Br 30 mol %), an equivalent weight amount of a silver chlorobromide (cubic particles whose base was the silver chloride and at portions of the surfaces of which 0.3 mol % silver bromide existed locally; average particle size: 0.7 μm; endowed with spectral sensitivity due to the addition of sensitizing dyes A, B and C each in an amount of $1.4 \times 10^{-4}$ mol per mol of silver halide) was used.

(Sensitizing dye A)

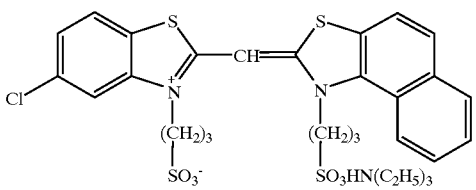

(Sensitizing dye B)

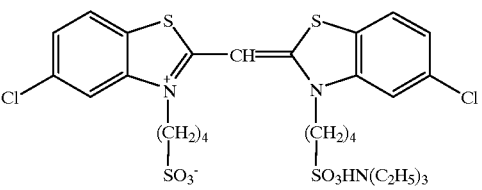

-continued (Sensitizing dye C)

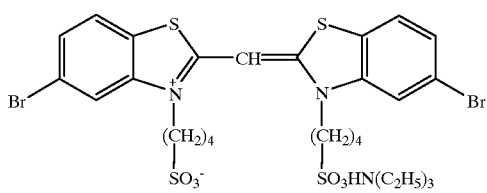

[Examples 5–8]

Samples 302–305 were prepared in the same manner as in Comparative Example 2 except that, in the emulsion of the coupler, instead of the comparative coupler (C-1), the coupler (2), (9), (31) or (37) was used, respectively.

The color image fastness evaluation test was carried out as follows. Each of the light-sensitive materials was wedge-exposed by white light and selected to the following processes.

| Process | Temperature | Processing Time |
|---|---|---|
| Color development | 38.5° C. | 45 seconds |
| Bleaching-fixing | 30–36° C. | 45 seconds |
| Stabilizing ① | 30–37° C. | 20 seconds |
| Stabilizing ② | 30–37° C. | 20 seconds |
| Stabilizing ③ | 30–37° C. | 20 seconds |
| Drying | 70–85° C. | 60 seconds |

In the processes of color developing, bleaching-fixing, stabilizing Ô, stabilizing 2̂, and stabilizing 3̂, processing was carried out by immersing the light-sensitive material in the corresponding processing solution as follows in accordance with the above-described conditions.

| (Color Developing Solution in Color Developing Process) | |
|---|---|
| water | 800 ml |
| dimethylpolysiloxane-based surfactant (silicone KF351A manufactured by Shinetsu Chemical Co., Ltd.) | 0.1 g |
| triethanolamine | 11.6 g |
| ethylenediaminetetraacetic acid | 4.0 g |
| sodium 4,5-dihydroxybenzene-1,3-disulfonate | 0.5 g |
| potassium chloride | 10.0 g |
| potassium bromide | 0.040 g |
| triazinylaminostilbene-based fluorescent whitening agent (Hakkor FWA-SF, manufactured by Showa Chemical Industry Co. Ltd.) | 2.5 g |
| sodium sulfite | 0.1 g |
| disodium-N,N-bis(sulfonateethyl)hydroxylamine | 8.5 g |
| monohydrate of N-ethyl-N-(β-methanesulfonamidoethyl)-3-methyl-4-aminoaniline 3/2 sulfate | 5.0 g |
| potassium carbonate | 26.3 g |
| add water until volume reaches | 1000 ml |
| pH (adjusted at 25° C. by potassium hydroxide and sulfuric acid | 10.15 |

| (Bleaching-Fixing Solution in Bleaching-Fixing Process) | |
|---|---|
| water | 800 ml |
| iron (III) ammonium ethylenediaminetetraacetate | 47.0 g |
| ethylenediaminetetraacetic acid | 1.4 g |
| m-carboxymethybenzenesulfinic acid | 8.3 g |
| nitric acid (67%) | 16.5 g |
| imidazole | 14.6 g |
| ammonium thiosulfate (750 g/liter) | 107 ml |
| ammonium sulfite | 16.0 g |
| potassium metabisulfite | 23.1 g |
| add water until volume reaches | 1000 ml |
| pH (adjusted at 25° C. by acetic acid and ammonia) | 6.0 |

| (Stabilizing Solutions in Stabilizing Process ① through ③) | |
|---|---|
| sodium isocyanurate chloride | 0.02 g |
| deionized water (conductivity 5 μs/cm or less) | 1000 ml |
| pH | 6.5 |

The respective samples obtained in tis way were irradiated for 14 days (intermittent irradiation with 5 hours of irradiation followed by one hour of darkness) by using a 100,000 Lux Xe light source.

The color formed density of each sample before and after the intermittent irradiation was carried out was measured by using a TCD densitometer manufactured by Fuji Photo Film Co., Ltd.. The ratio of the color formed density after the irradiation to the color formed density before the irradiation (ie., the remaining ratio which is expressed as a percentage) was calculated, and was used as an index for evaluating the color image fastness. The results are shown in following Table 4.

TABLE 4

| Sample No. | Coupler | Remaining Ratio | Notes |
|---|---|---|---|
| Comp. Example 2 | 301 | Comparative coupler (C-1) | 45 | Comparative example |
| Example 5 | 302 | Coupler (2) | 72 | Present invention |
| Example 6 | 303 | Coupler (9) | 65 | Present invention |
| Example 7 | 304 | Coupler (31) | 60 | Present invention |
| Example 8 | 305 | Coupler (37) | 58 | Present invention |

As is clear from Table 4, even if the types of emulsions or processing factors are varied, the samples 302 through 305 using the couplers of the present invention exhibit excellent light fastness.

[Example 9]

A light-sensitive material was prepared which was the same as Sample 404 of Example 4 of JP-A-11-282108, except that the yellow coupler ExY in the first layer of sample 404 was replaced, in an equivalent molar amount, with coupler (1) of the present invention. This light-sensitive material was subjected to exposure and developing processing in accordance with the methods described in Example 4 of JP-A-11-282108. The light-sensitive material was then evaluated in accordance with the methods described in the Examples of the present application, and results similar to those of Example 1 of the present application were achieved.

[Example 10]

A light-sensitive material was prepared which was the same as Sample 101 in JP-A-11-305396 except that ExY-2 and ExY-3 in the thirteenth layer and the fourteenth layer were both replaced, in equivalent molar amounts, with coupler (1) of the present invention. This light-sensitive material was exposed and subjected to developing processing in accordance with the methods described in Example 1 of JP-A-11-305396. The light-sensitive material was then evaluated in accordance with the methods described in the Examples of the present application, and results similar to those of Example 1 of the present application were achieved.

[Example 11]

A light-sensitive material was prepared which was the same as Sample 107 in Example 1 of JP-A-11-84601, except that the couplers C-5, C-6 and C-10 of the thirteenth layer and the fourteenth layer and the couplers C-6 and C-10 of the fifteenth layer were replaced, in equivalent molar amounts, with coupler (1) of the present invention. This light-sensitive material was exposed and subjected to developing processing in accordance with the methods described in Example 1 of JP-A-11-84601. The light-sensitive material was then evaluated in accordance with the methods described in the Examples of the present application, and results similar to those of Example 1 of the present application were achieved.

What is claimed is:

1. A silver halide photographic light-sensitive material comprising a support and at least one light-sensitive layer formed on the support, wherein at least one of said light-sensitive layers contains at least one of couplers represented by following formula (I):

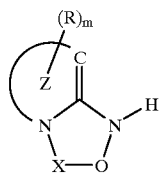

(I)

wherein Z represents an atomic group that comprises a carbon atom and/or a nitrogen atom which, together with N—C=C, form a 5- or 6-member aromatic ring; R represents a substituent, and when there are a plurality of R, the R can be same or different, and may be coupled to each other so as to form a fused ring; m represents an integer of from 1 to 4; and X represents a carbonyl group, a methylene group, or a >C=N—Rn group wherein Rn represents a substituent.

2. A silver halide photographic light-sensitive material according to claim 1, wherein the ring formed by Z and N—C=C in the coupler represented by formula (I) is selected from the group consisting of a pyrrole ring, a pyrazole ring, an imidazole ring, a 1,2,3-triazole ring, a pyridine ring, a pyridazine ring, a pyrimizine ring, a pyrazine nng, an indole ring, an isoindole ring, a benzimidazole ring, a quinoline ring, and an isoquinoline ring.

3. A silver halide photographic light-sensitive material according to claim 1, wherein the coupler represented by said formula (I) is at least one of couplers represented by following formulas (II), (III), (IV), or (V):

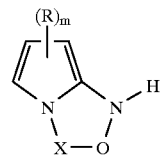

(II)

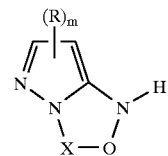

(III)

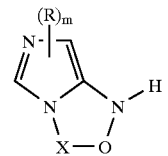

(IV)

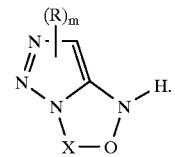

(V)

4. A silver halide photographic light-sensitive material according to claim 1, wherein X of the coupler represented by formula (I) is a carbonyl group.

5. A silver halide photographic light-sensitive material according to claim 1, wherein the amount of the coupler contained in the silver halide photographic light-sensitive material ranges from $1\times10^{-3}$ mol to 1 mol per 1 mol of silver halide.

6. A silver halide photographic light-sensitive material according to claim 3, wherein the coupler represented by formula (I) is selected from the group consisting of couplers represented by formula (III) and couplers represented by formula (V).

* * * * *